(12) United States Patent
Munro, III

(10) Patent No.: US 7,276,716 B1
(45) Date of Patent: Oct. 2, 2007

(54) SHIELDED TREATMENT ENVIRONMENT FOR BRACHYTHERAPY SOURCE

(75) Inventor: John J. Munro, III, North Andover, MA (US)

(73) Assignee: Implant Sciences Corporation, Wakefield, MA (US)

( * ) Notice: Subject to any disclaimer, the term of this patent is extended or adjusted under 35 U.S.C. 154(b) by 462 days.

(21) Appl. No.: 10/997,050

(22) Filed: Nov. 24, 2004

(51) Int. Cl.
*G21F 3/00* (2006.01)

(52) U.S. Cl. ............................ 250/515.1; 250/519.1

(58) Field of Classification Search ............ 250/515.1, 250/519.1, 517.1; 378/203
See application file for complete search history.

(56) References Cited

U.S. PATENT DOCUMENTS

| | | | |
|---|---|---|---|
| 1,907,523 A | 5/1933 | Egressi et al. |
| 3,299,270 A | 1/1967 | D'Avella |
| 3,308,297 A | 3/1967 | Mansker |
| 3,924,374 A | 12/1975 | Volper |
| 4,062,518 A | 12/1977 | Stivender et al. |
| 4,074,141 A | 2/1978 | Bryant |
| 4,400,623 A | 8/1983 | Jacobson |
| 4,581,538 A | 4/1986 | Lenhart |
| 4,638,166 A | 1/1987 | Baudro |
| 4,729,869 A | 3/1988 | Schukei et al. |
| 5,006,718 A | 4/1991 | Lenhart |
| 5,090,044 A | 2/1992 | Kobayashi |
| 5,417,225 A | 5/1995 | Rubenstein et al. |
| 5,981,964 A | 11/1999 | McAuley et al. |
| 6,325,538 B1 | 12/2001 | Heesch |
| 6,653,648 B2 | 11/2003 | Goldstein |
| 7,057,194 B2 * | 6/2006 | Goldstein ................ 250/515.1 |
| 2005/0236588 A1 * | 10/2005 | Ein-Gal ................... 250/515.1 |

* cited by examiner

*Primary Examiner*—Kiet T. Nguyen
(74) *Attorney, Agent, or Firm*—Muirhead and Saturnelli, LLC (57) ABSTRACT

A radiation protection system for shielding medical personnel from a gamma ray source being used to provide brachytherapy to a patient is provided by disposing shielding material between the source of radiation and locations outside the radiation protection system in such a manner as to provide shielding for the primary radiation in directions from which radiation from the source may emerge, while providing the patient an open viewing area with a large field of view for the patient to view the locations outside the radiation protection system. The described system reduces the radiation exposure of staff in the treatment room, thereby permitting physicians and therapists to observe the patient without being exposed to excessive amounts of radiation. The opening in the radiation protection system around the head of the patient provides the ability for the patient to see his surroundings and to eliminate the anxiety resulting from the feeling of being closed in.

17 Claims, 7 Drawing Sheets

SHIELDED TREATMENT ENVIRONMENT FOR BRACHYTHERAPY SOURCE

BACKGROUND OF THE INVENTION

1. Technical Field

This system described herein relates generally to radiation protection systems and, more particularly, to radiation shielding systems integrated into procedural environments for use in the course of therapeutic procedures, for example, to radiation shielding systems integrated into procedural environments for use in the course of the performance of brachytherapy procedures as well as methods for the use of such systems.

2. Description of Related Art

Various techniques have been developed to treat tumors in the body. In general, the use of radiation to reduce or eliminate malignancy has been known for many years.

Brachytherapy is a method of radiation treatment of cancerous tissue in which the radiation source is placed in or near the cancerous tissue. Brachytherapy treatment permits administration of higher radiation dose to the tumor with better sparing of surrounding normal healthy tissues.

Temporary brachytherapy is a process whereby the radioactive sources are placed into the body, usually using an applicator, such as a needle, catheter or other tubular apparatus, for a limited period of time to deliver the requisite radiation dose, and then the sources are removed. With this treatment modality, applicators are prepositioned in the patient. The sources are later temporarily placed within them. This procedure is known as "afterloading".

Temporary brachytherapy has been performed using a technique called "Low Dose Rate Brachytherapy". Using this technique, radioactive sources are applied to provide a dose rate of 0.4 to 2 Gy/hour to the tumor. Using these techniques, treatment could require up to several days, during which period the patient remained hospitalized. Low dose rate techniques utilized a variety of radioactive isotopes, including $^{125}$Iodine, $^{137}$Cesium, $^{198}$Gold and $^{192}$Iridium.

There is also a technique for "High Dose Rate Brachytherapy" which uses a source to provide dose rates in the range of 2-7 Gy/minute. This technique permits the treatment to be performed in less than an hour, and without the hospitalization of the patient. Treatments may be delivered in multiple fractions over several days or weeks.

This high dose rate brachytherapy method employs a highly radioactive source that may be delivered via a catheter or other applicator appliance through a natural cavity, duct or vessel of the body directly to the tumor site for localized irradiation.

High dose rate brachytherapy may be performed using $^{192}$Iridium sources which have an initial activity of ~10 Curies, although other radionuclides such as $^{169}$Ytterbium and $^{60}$Cobalt may be used. Such sources may produce dose rates of 6.8 Gy/min at 1 centimeter. Using such a source, high dose rate treatments may be 5-15 minutes duration.

Because of the very high dose rates associated with these sources, high dose rate brachytherapy treatments are often performed in shielded facilities to provide radiation protection to and reduce the radiation exposure of radiation oncologists, physicists, attending physicians, nurses, and other allied health personnel. Because of the panoramic emission pattern of the radiation from these high dose rate brachytherapy sources, this shielding may be designed to completely surround the radiation source.

These treatments may be performed in large shielded rooms with shielding on all sides as well as the floor and ceiling. Access to these rooms may be through large, heavy shielded doors, or through "maze"-type entrances. These rooms may require large amounts of floor space to house the patient, the treatment device and the treatment personnel who prepare the patient for treatment. Because of the large size of these rooms, the rooms may require an enormous amount of shielding material, which results in a relatively high cost.

It would be very attractive to provide this shielding in a more localized manner, as the volume of shielding required becomes less as the shielding is moved closer to the source of the radiation. It is therefore desirable to provide an improved design and method of fabrication and use for a shielded environment for the performance of temporary brachytherapy which would reduce the area required for its use, reduce the volume of shielded material required, and reduce the cost.

A fast growing application of high dose rate brachytherapy is accelerated partial breast irradiation (APBI), where a patient receives two fractions per day over a five-day period. The large number of prospective patients for this treatment protocol could tax the availability of existing treatment facilities, and could require the construction of new dedicated shielded treatment rooms. The shielding advantage of a localized shielding environment could facilitate the performance of breast brachytherapy in a much more moderately shielded room.

Of course, this could be accomplished by essentially "shrinking" the size of the room to a size just larger that the dimensions of the patient, essentially creating a shielded box around the patient. This could have the adversely effect of the comfort of the patient, by making the patient feel "closed in", creating apprehension much like that one experiences during a closed magnetic resonance imaging examination. Therefore, it would be desirable to provide shielding in such a manner as to provide a visual open field of view to the patient beyond the shielding to reduce apprehension associated with a "closed-in" feeling.

Localized shielding environments have been used for other diagnostic and therapeutic applications, but none of these is arguably suitable for the very high radiation exposure rates and high gamma ray energies encountered in high dose rate brachytherapy.

Both fixed and mobile lead shields are employed in fluoroscopic procedures to minimize radiation exposure. Such shields may be constructed of radiation resistant plates that are interposed between the operators and the patient on an x-ray table. Despite the use of these shields, medical personnel are still exposed to radiation. Consequently, personnel also wear leaded protective clothing (including full lead aprons, thyroid collars and leaded glasses). These types of devices and clothing may not provide suitable or sufficient shielding for the very high radiation exposure rates and high gamma ray energies encountered in high dose rate brachytherapy.

There are patents teaching systems for protecting and shielding against radiation in x-ray laboratories, including various shields made of radiation resistant material that are either mobile or attached to the x-ray table and can be adjusted between the operators and the x-ray source. Such systems are described in various U.S. patents, including the following:

Egressi and Huszar, U.S. Pat. No. 1,907,523
D'Avella, U.S. Pat. No. 3,299,270
Mansker, U.S. Pat. No. 3,308,297

Volper, U.S. Pat. No. 3,924,374
Stivender, Lang and Mentink, U.S. Pat. No. 4,062,518
Bryant, U.S. Pat. No. 4,074,141
Lenhart, U.S. Pat. No. 4,581,538
Baudro, U.S. Pat. No. 4,638,166
Schukei and McDonald, U.S. Pat. No. 4,729,869
Lenhart, U.S. Pat. No. 5,006,718
Kobayashi, U.S. Pat. No. 5,090,044
Rubenstein, Pahira, and Taylor, U.S. Pat. No. 5,417,225
McAuley and Geiger, U.S. Pat. No. 5,981,964
Heesch, U.S. Pat. No. 6,325,538, and
Goldstein, U.S. Pat. No. 6,653,648

Though there are numerous shapes and designs for shields, and although the shields may be constructed of various materials, the systems described in the patents listed above are all arguably directed to providing shielding from a source of radiation external to the patient and do not sufficiently protect against radiation exposure from a radiation source located within the patient. Accordingly, it is desirable to sufficiently reduced the primary and secondary radiation exposure of medical personnel in the vicinity of a patient undergoing high dose rate brachytherapy through the placement of very high exposure rate sources within the patient's body, and in particular, in such a way as to provide the patient with a wide field of view of the area outside the shielding.

SUMMARY OF THE INVENTION

It is in view of the above that the present invention was developed. The invention relates to a radiation protection system for shielding medical or other personnel from a gamma ray source (or other radiation) being used to provide radiation therapy (brachytherapy) to a patient by disposing shielding material between the source of radiation and locations outside the radiation protection system in such a manner as to provide shielding for the primary radiation in all directions from which radiation from the source may emerge, while providing the patient an open viewing area with a large field of view for the patient to view the locations outside the radiation protection system.

The system described herein is designed to reduce the radiation exposure of staff in the treatment room.

The system described herein is also designed to substantially reduce exposure to primary radiation around a treatment platform and thereby permitting physicians and therapists to observe the patient without being exposed to excessive amounts of radiation.

The system described herein is also designed to reduce exposure to secondary radiation in the region around a treatment platform where medical professionals operate on a patient.

The system described herein is also designed so that the opening around the head of the patient which provides the ability for the patient to see his or her surroundings and to reduce the feeling of being closed in.

One embodiment of the system described herein is a radiation protection system for shielding medical personnel from a gamma ray source being used to provide brachytherapy to a patient. The system includes a table having a radiation-shielded top surface for supporting a patient; a radiation-shielded enclosure surrounding the girth of the patient, and radiation shielded end enclosures providing radiation shielding in the direction of the head and feet of the patient.

Further features and advantages of the system described herein, as well as the structure and operation of various embodiments, are described in detail below with reference to the accompanying drawings.

DETAILED DESCRIPTION OF VARIOUS EMBODIMENTS

Figure 1A:
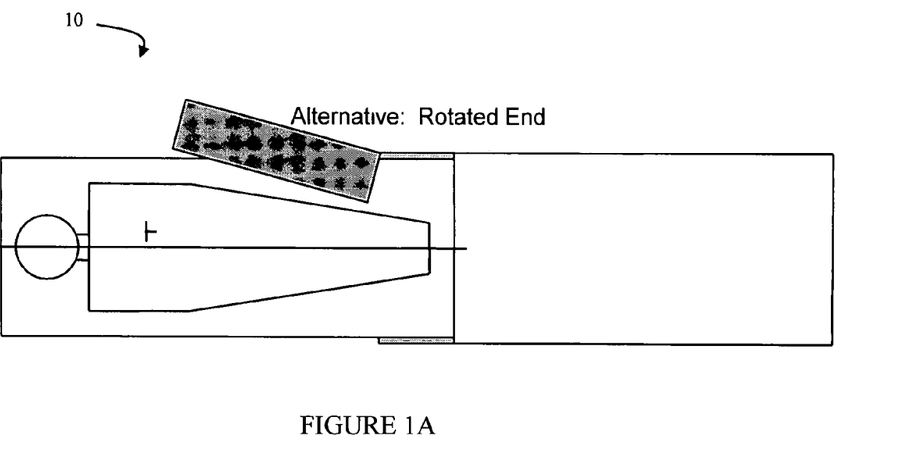
FIGS. 1A, 1B, and 1C, 1D, and 1E illustrate a radiation protection system that covers a patient on a treatment platform in the form of a table designed for breast brachytherapy procedures in which the patient is in a supine position according to the system described herein.
Figure 1B:
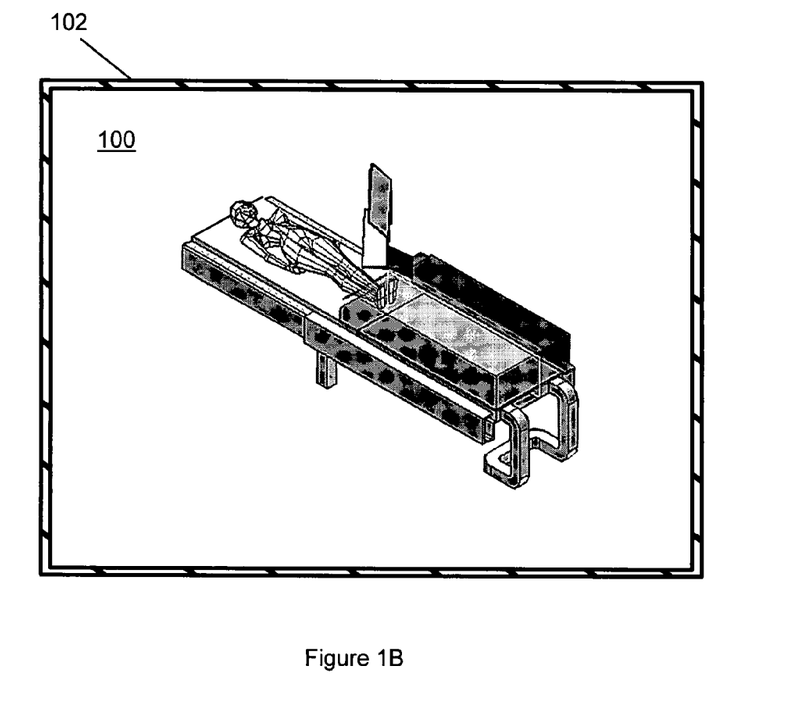
Figure 1C:
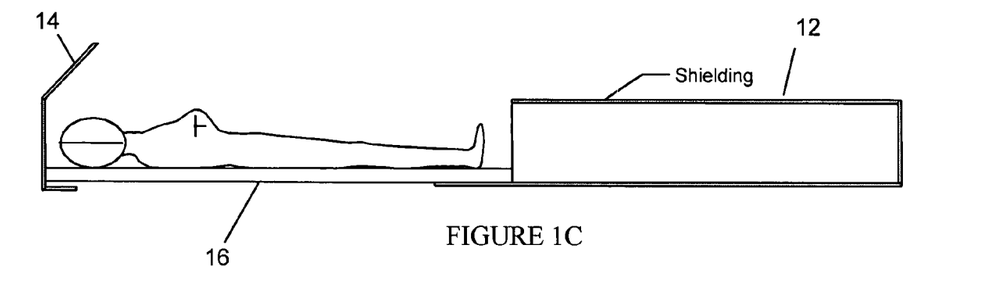
Figure 1D:
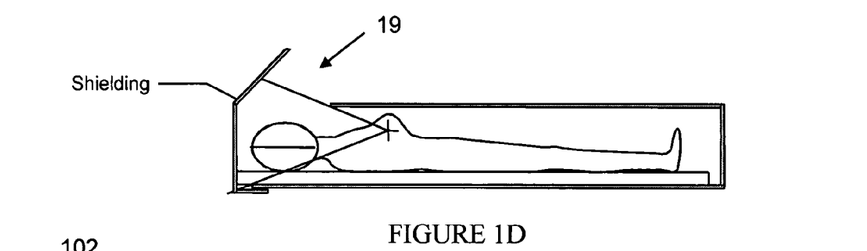
Figure 1E:
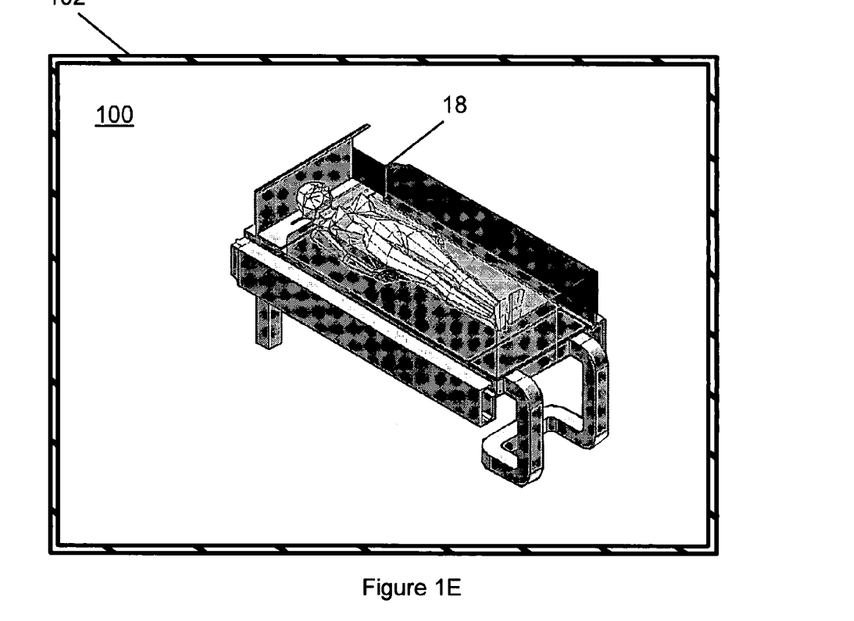
Figure 2A:
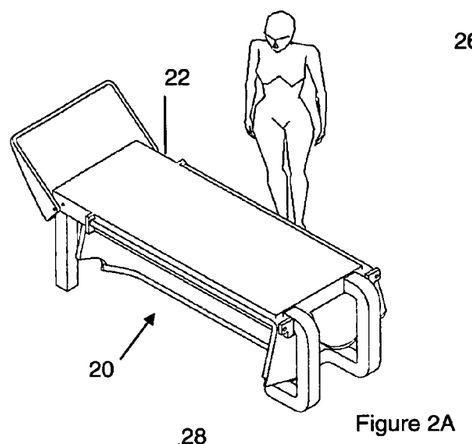
FIGS. 2A, 2B, 2C, 2D, and 2E illustrate another embodiment of a radiation protection system that covers a patient on a treatment platform in the form of a table designed for breast brachytherapy procedures in which the patient is in a supine position according to the system described herein.
Figure 2B:
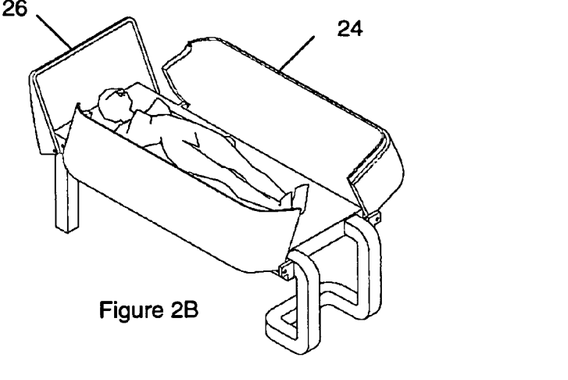
Figure 2C:
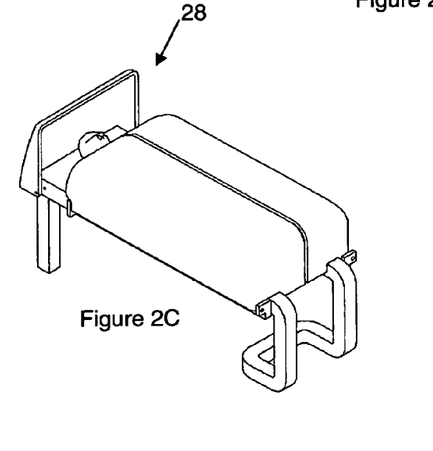
Figure 2D:
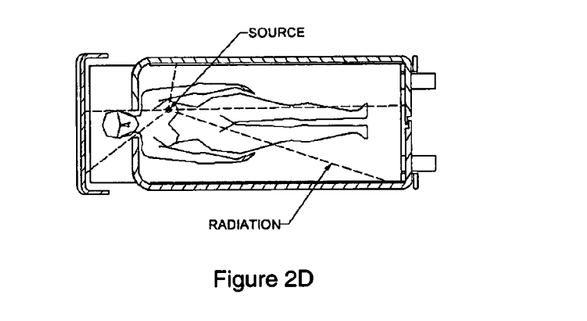
Figure 2E:
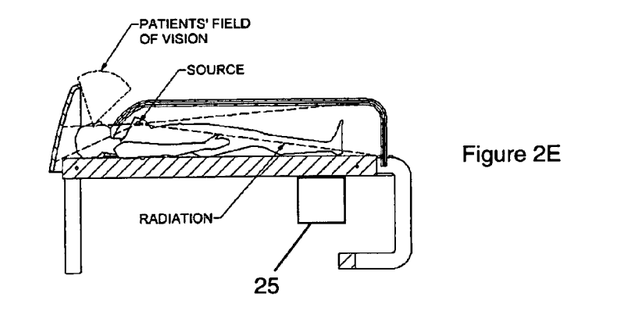
Figure 3A:
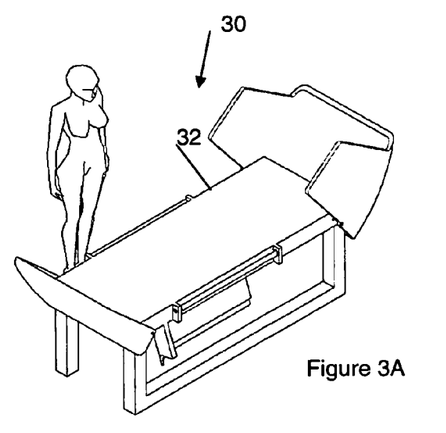
FIGS. 3A, 3B, 3C, 3D, and 3E illustrate another embodiment of a radiation protection system that covers a patient on a treatment platform in the form of a table designed for breast brachytherapy procedures in which the patient is in a supine position according to the system described herein.
Figure 3B:
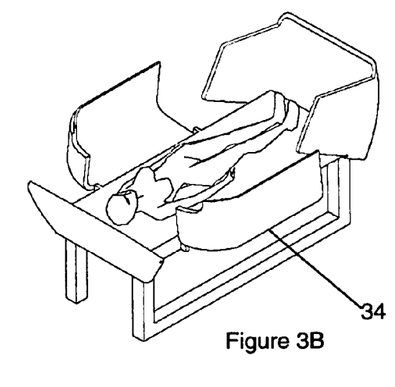
Figure 3C:
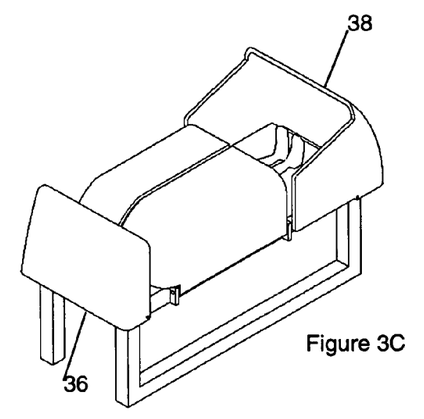
Figure 3D:
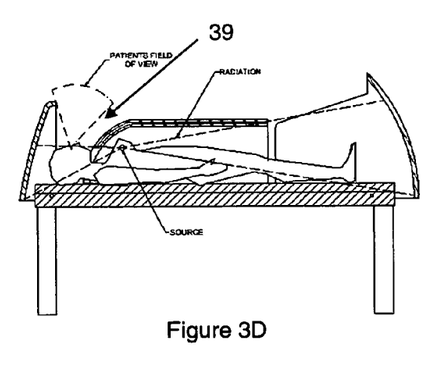
Figure 3E:
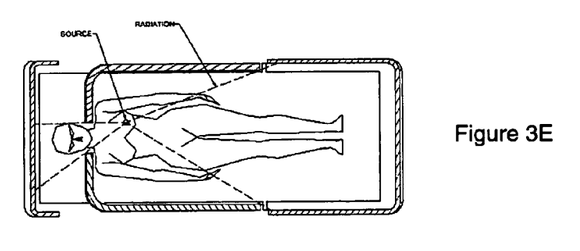
Figure 4A:
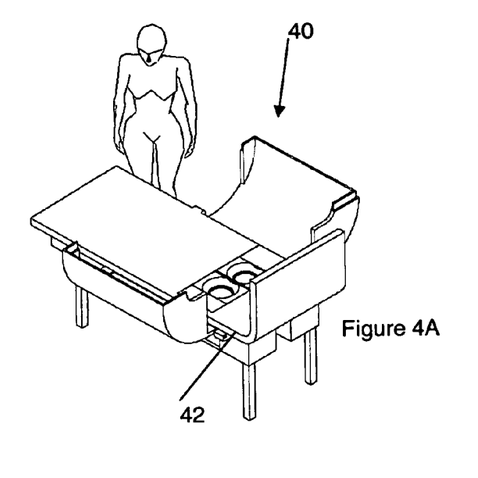
FIGS. 4A, 4B, 4C, 4D, and 4E illustrate another embodiment of a radiation protection system that covers a patient on a treatment platform in the form of a table designed for breast brachytherapy procedures in which the patient is in a prone position according to the system described herein.
Figure 4B:
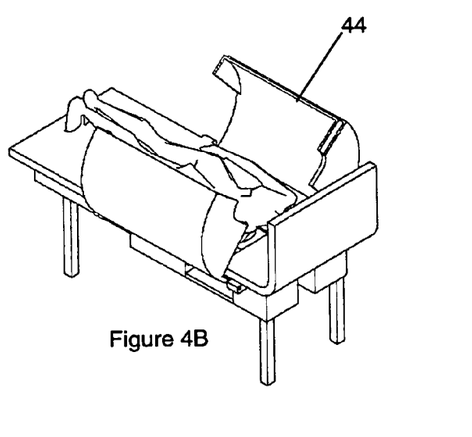
Figure 4C:
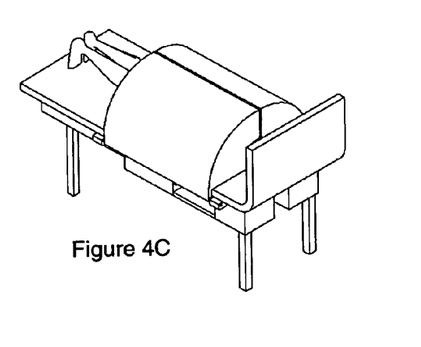
Figure 4D:
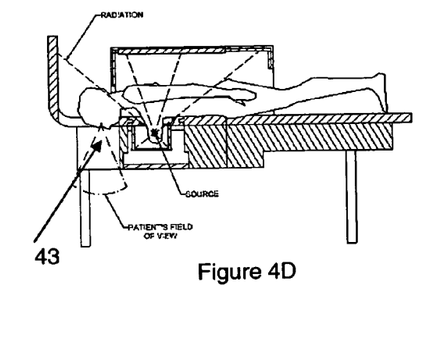
Figure 4E:
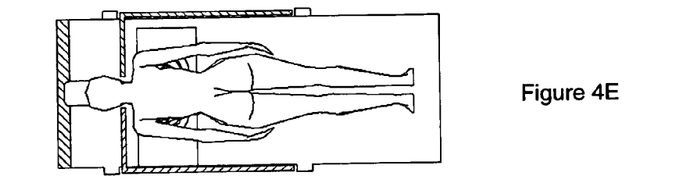
Figure 5A:
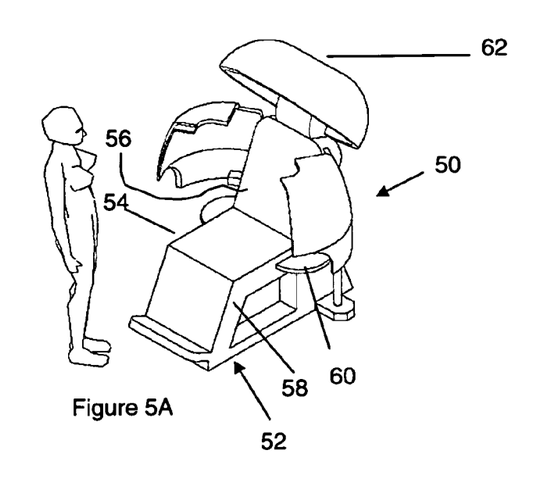
FIGS. 5A, 5B, 5C, 5D, and 5E illustrate another embodiment of a radiation protection system that covers a patient on a treatment platform in the form of a chair designed for breast brachytherapy procedures in which the patient is in a seated position according to the system described herein.
Figure 5B:
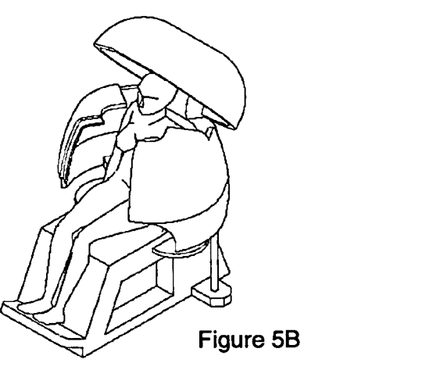
Figure 5C:
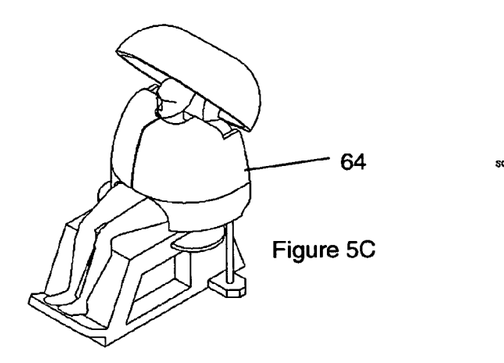
Figure 5D:
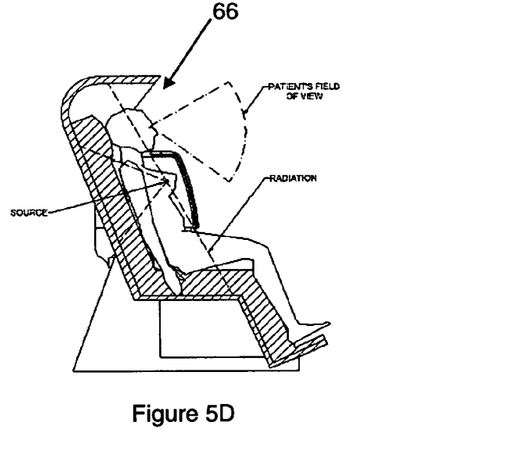
Figure 5E:
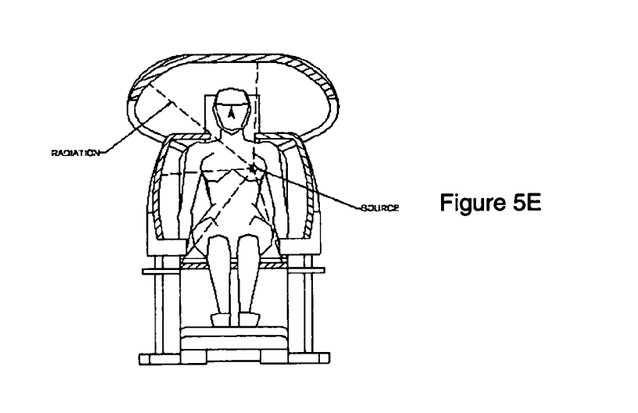

FIGS. 1A-1E illustrate a radiation protection system 10 that covers a patient on a treatment platform in the form of a table designed for breast brachytherapy procedures in which the patient is in a supine position. In one embodiment, the radiation protection system 10 includes a shielded tunnel 12. Each side of the shielded tunnel 12 is provided with sufficient lead or other shielding material to provide sufficient protection to adjacent personnel. A shielded cap 14 at the head, which may be motorized, pivots into place once the patient is positioned, providing shielding in the superior direction (FIGS. 1A, 1B). In an alternative embodiment, shielded cap 14 may be disposed at the head of table 15 (FIG. 1C). Cap 14 may be fixed in place or may be hingely attached to table 16, so that it may be positioned after the patient is in position. The elements 12, 14 may provide shielding for the primary radiation in the directions from which health care providers or others may approach the patient. FIGS. 1D and 1E depict the radiation protection system after deployment of the shielded tunnel 12 and cap 14. A cowl 18 may be disposed at the end of tunnel 12 to further shield medical personnel. A gap 19 between the tunnel 12 and the cap 14 provides the patient with a large field of view to reduce anxiety of being totally enclosed. In one embodiment, the field of view encompasses an included angle of at least thirty degrees, at least forty degrees, or at least fifty degrees in the lateral plane, vertical plane, or both.

In an alternative embodiment, the field of view encompasses an included angle of at least ten degrees or at least twenty degrees. The scattered radiation emerging from the system when used with a high dose rate brachytherapy source may be less than fifty milliroentgens per hour at one meter from the system. The scattered radiation may be reduced to less than two milliroentgen per hour with the addition of one millimeter of lead, for example, as inherent shielding 102 in the walls of a diagnostic room, or, more generally, disposed in any appropriate fashion about the periphery of the area 100 in which the radiation protection system is situated. Alternatively, lead foil may be used.

FIGS. 2A, 2B, 2C, 2D, and 2E illustrate a radiation protection system 20 that covers a patient on a treatment platform in the form of a table designed for breast brachytherapy procedures in which the patient is in a supine position. In this embodiment, the radiation protection system includes four shielded elements, each shielded with sufficient lead or other shielding material to provide sufficient protection to adjacent personnel. A base 22 of the treatment table provides shielding in the downward direction. Two clam-shell shaped segments 24 pivot over the patient's torso and legs after the patient is positioned on the treatment table to provide shielding in the upward, lateral and caudal directions. A motor 25 may used to manipulate clam-shell shaped segments 24 once the patient is in position. A shielded cap 26 at the head, which also may be motorized, may also pivot into place once the patient is positioned, providing shielding in the superior direction. The segments 22, 24, 26 may provide shielding for the primary radiation in the directions from which health care providers or others may approach the patient. A gap 28 between the cap 26 and the clam-shell shaped segments 24 provides the patient with a large field of view to reduce anxiety of being totally enclosed. The scattered radiation emerging from the system when used with a high dose rate brachytherapy source may be less than fifty milliroentgens per hour at one meter from the system. The scattered radiation may be reduced to less than two milliroentgen per hour with the addition of one millimeter of lead, for example, as inherent shielding in the walls of a diagnostic room, or, more generally, disposed in any appropriate fashion about the periphery of the area in which the radiation protection system is situated. Alternatively, lead foil may be used.

FIGS. 3A, 3B, 3C, 3D, and 3E illustrate a radiation protection system 30 that covers a patient on a treatment platform in the form of a table designed for breast brachytherapy procedures in which the patient is in a supine position. In this embodiment, the radiation protection system includes five shielded elements, each shielded with sufficient lead or other shielding material to provide sufficient protection to adjacent personnel. A base 32 of the treatment table provides shielding in the downward direction. Two clam-shell shaped segments 34 pivot over the patient's midsection (torso and upper leg) after the patient is positioned on the treatment table to provide shielding in the upward and lateral directions. The segments 34 may be motorized to facilitate manipulating once the patient is in position. Two shielded caps 36, 38, at the head and foot of the table, respectively, may pivot into place once the patient is positioned and may also be motorized. The segments 32, 34, 36, 38 may provide shielding for the primary radiation in the directions from which health care providers or others may approach the patient. A gap 39 between the head cap 36 and the clam-shell shaped segments 34 provides the patient with a large field of view, to reduce anxiety of being totally enclosed. The scattered radiation emerging from the system when used with a high dose rate brachytherapy source may be less than fifty milliroentgens per hour at one meter from the system. The scattered radiation may be reduced to less than two milliroentgen per hour with the addition of one millimeter of lead, for example, as inherent shielding in the walls of a diagnostic room, or, more generally, disposed in any appropriate fashion about the periphery of the area in which the radiation protection system is situated. Alternatively, lead foil may be used.

FIGS. 4A, 4B, 4C, 4D, and 4E illustrate another embodiment of a radiation protection system 40 that covers a patient on a treatment platform in the form of a table designed for breast brachytherapy procedures in which the patient is in a prone position. In this embodiment, the radiation protection system 40 includes three shielded elements, each shielded with sufficient lead, or other shielding material to provide sufficient protection to adjacent personnel. A well 42 of the table provides shielding in the downward and lateral directions. A gap 43 in the well 42 provides a space from which the patient may see the surrounding room. Two clam-shell shaped segments 44 pivot over the patient's midsection (over the patient's back) after the patient is positioned on the table to provide shielding in the upward and lateral directions. The segments 44 may be motorized to facilitate manipulating once the patient is in position. The segments 42, 44 may provide shielding for the primary radiation in the directions from which health care providers or others may approach the patient. The gap 43 provides the patient with a large field of view, to reduce anxiety of being totally enclosed. The scattered radiation emerging from the system when used with a high dose rate brachytherapy source may be less than fifty milliroentgens per hour at one meter from the system. The scattered radiation may be reduced to less than two milliroentgen per hour with the addition of one millimeter of lead, for example, as inherent shielding in the walls of a diagnostic room, or, more generally, disposed in any appropriate fashion about the periphery of the area in which the radiation protection system is situated. Alternatively, lead foil may be used.

FIGS. 5A, 5B, 5C, 5D, and 5E illustrate another embodiment of a radiation protection system 50 that covers a patient on a treatment platform in the form of a chair designed for breast brachytherapy procedures in which the patient is in a seated position. In this embodiment, the radiation protection system includes three shielded elements, each shielded with sufficient lead or other shielding material to provide sufficient protection to adjacent personnel. A body 52 of the chair, including a seat 54, a back 56, a leg support 58, sides 60, and a cover 62, provide shielding in the downward, lateral and upward directions. Two clam-shell shaped segments 64 pivot over the patient's breast area after the patient is positioned in the chair to provide shielding in the forward and lateral directions. The segments 64 may be motorized to facilitate manipulating once the patient is in position. The segments 52, 54, 56, 58, 60, 62, 64 provide shielding for the primary radiation in the directions from which health care providers or others may approach the patient. A gap 66 between the cover 62 and the clam-shell shaped segments 64 provides the patient with a large field of view to reduce anxiety of being totally enclosed. The scattered radiation emerging from the system when used with a high dose rate brachytherapy source may be less than fifty milliroentgens per hour at one meter from the system. The scattered radiation may be reduced to less than two milliroentgen per hour with the addition of one millimeter of lead, for example, as inherent shielding in the walls of a diagnostic room, or, more generally, disposed in any appropriate fashion about the periphery of the area in which the radiation protection system is situated. Alternatively, lead foil may be used.

Figure 6:
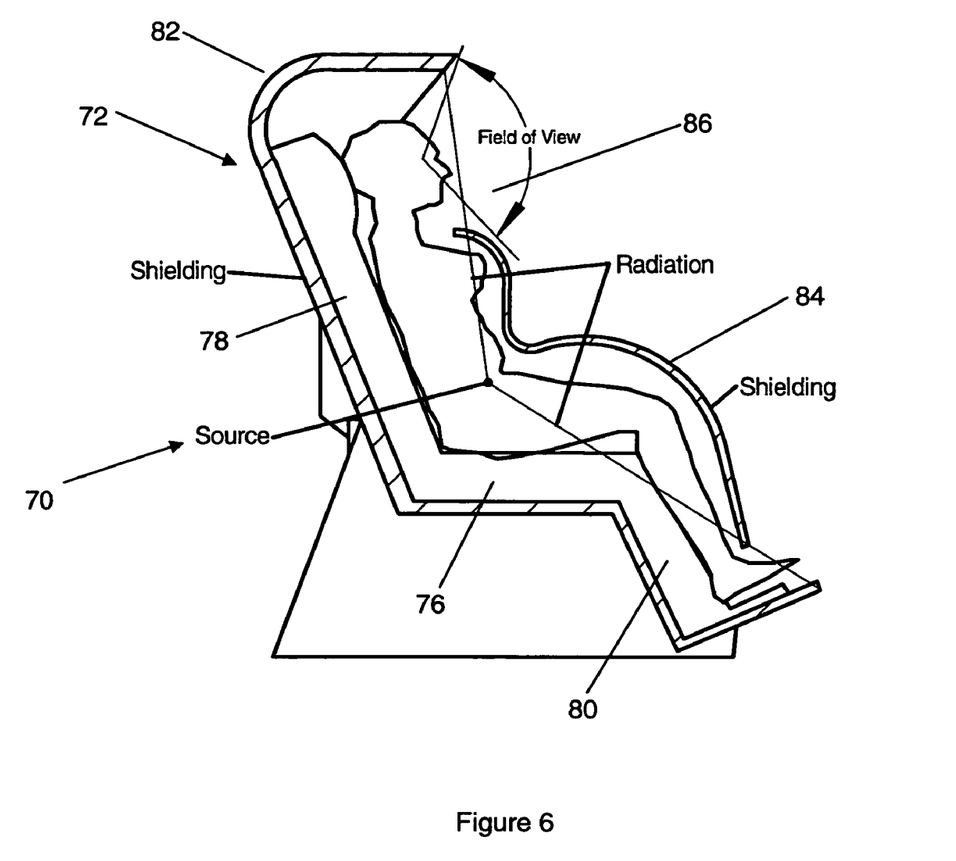
FIG. 6 illustrates another embodiment of a radiation protection system that covers a patient on a treatment platform in the form of a chair designed for brachytherapy procedures in which the patient is in a seated position according to the system described herein.

FIG. 6 illustrates another embodiment of a radiation protection system 70 that covers a patient on a treatment platform in the form of a chair 72 designed for gynecological treatments procedures in which the patient is in a seated position. In this embodiment, the radiation protection system includes three shielded elements, each shielded with sufficient lead or other shielding material to provide sufficient protection to adjacent personnel. The body of the chair, including a seat 76, back 78, leg support 80, sides (not shown) and cover 82, may provide shielding in the downward, lateral and upward directions. Two clam-shell shaped segments similar to those shown in FIG. 5 pivot over the patient's midsection area (torso and lap) after the patient is positioned in the chair to provide shielding 84 in the forward, lateral and upward directions. The segments may be motorized to facilitate manipulating once the patient is in position. The segments provide shielding for the primary radiation in the directions from which health care providers may approach the patient. With nothing around the head, the patient has a large field of view 86 to reduce anxiety of being totally enclosed. The scattered radiation emerging from the system when used with a high dose rate brachytherapy source may be less than fifty milliroentgens per hour at one meter from the system. The scattered radiation may be reduced to less than two milliroentgen per hour with the addition of one millimeter of lead, for example, as inherent shielding in the walls of a diagnostic room, or, more generally, disposed in any appropriate fashion about the periphery of the area in which the radiation protection system is situated. Alternatively, lead foil may be used.

The shapes of various elements illustrated herein may be altered without departing from the spirit and scope of the invention. The shielding material may be one of lead, steel, tungsten, brass, concrete, and combinations of any of these materials and/or any other suitable material. The system described herein may be used for shielding any type or combination of types of radiation, in addition to the gamma ray shielding described herein.

While the invention has been disclosed in connection with various embodiments, modifications thereon will be readily apparent to those skilled in the art. Accordingly, the spirit and scope of the invention is set forth in the following claims.

What is claimed is:

1. A radiation protection system, comprising:
    shielding material disposed between a source of radiation and locations outside the radiation protection system to provide shielding for primary radiation along predetermined directions in which radiation from the source may emerge; and
    an open viewing area provided in the shielding material from which locations outside the radiation protection system are viewable from within the radiation protection system, wherein the shielding material includes a shielded table providing shielding in a downward direction, two clam-shell shaped segments that pivot over a supine patient's midsection and legs to provide shielding in upward and lateral directions and in a direction of the feet, and a shielded cap that pivots over a patient's head.

2. The radiation protection system of claim 1, wherein the shielding material includes a shielded tunnel providing shielding in upward and lateral directions.

3. The radiation protection system of claim 2, wherein the shielded cap is hingedly attached to the shielded tunnel.

4. The radiation protection system of claim 2, wherein the shielded cap is hingedly attached to a table over which the shielded tunnel is disposed.

5. The radiation protection system of claim 1, wherein the shielding material includes two shielded caps that pivot over the patient's head and feet.

6. The radiation protection system of claim 1, wherein the shielding material is selected from the group consisting of lead, steel, tungsten, brass, concrete, and combinations of any of these materials.

7. The radiation protection system of claim 1, wherein the field of view encompasses an included angle of at least thirty degrees in a lateral plane.

8. The radiation protection system of claim 1, wherein the field of view encompasses an included angle of at least thirty degrees in a vertical plane.

9. The radiation protection system of claim 1, wherein the shielding material includes shielded elements that are moveable between a closed position and an open position.

10. The radiation protection system of claim 9 wherein the shielded elements are equipped with an actuation device to provide power for moving the elements.

11. A radiation protection system, comprising:
    shielding material disposed between a source of radiation and locations outside the radiation protection system to provide shielding for primary radiation along predetermined directions in which radiation from the source may emerge; and
    an open viewing area provided in the shielding material from which locations outside the radiation protection system are viewable from within the radiation protection system, wherein the shielding material includes a well providing shielding in downward and lateral directions and two clam-shell shaped segments that pivot over a midsection of a prone patient positioned on a shielded table, providing shielding in upward and lateral directions.

12. A radiation protection system, comprising:
    shielding material disposed between a source of radiation and locations outside the radiation protection system to provide shielding for primary radiation along predetermined directions in which radiation from the source may emerge; and
    an open viewing area provided in the shielding material from which locations outside the radiation protection system are viewable from within the radiation protection system, wherein the shielding material includes a chair having a shielded seat, back, leg support, sides and cover, providing shielding in downward, lateral and upward directions, and two clam-shell shaped segments that pivot over a breast area of a patient seated in the chair, providing shielding in forward and lateral directions.

13. The radiation protection system of claim 12 wherein the two clam-shell shaped segments pivot over a seated patient's lap providing shielding in the forward, lateral and upward directions.

14. A radiation protection system, comprising:
    shielding material disposed between a source of radiation and locations outside the radiation protection system to provide shielding for primary radiation along predetermined directions in which radiation from the source may emerge; and
    an open viewing area provided in the shielding material from which locations outside the radiation protection system are viewable from within the radiation protection system, wherein the radiation exposure rate at one meter from the system is less than fifty milliroentgens per hour when a high dose rate brachytherapy source is disposed within the system.

15. The radiation protection system of claim 14 in which about one millimeter of lead is disposed about the periphery of an area in which the radiation protection system is situated.

16. The radiation protection system of claim 14, further comprising:
a layer of about one millimeter of lead disposed on a surface of the shielding material, in which the scattered radiation exposure rate at one meter from the system when a high dose rate brachytherapy source is disposed within the system is less than two milliroentgen per hour.

17. The radiation protection system of claim 15, wherein the about one millimeter of lead is disposed in walls of a room in which the radiation protection system is situated.

* * * * *